United States Patent [19]

Giersch et al.

[11] Patent Number: 4,524,019
[45] Date of Patent: Jun. 18, 1985

[54] SPIRO-LACTONE DERIVATIVES, THEIR USE AS PERFUMING AGENTS, AND PERFUMING COMPOSITION CONTAINING SAME

[75] Inventors: Wolfgang K. Giersch; Günther Ohloff, both of Bernex, Switzerland

[73] Assignee: Firmenich, SA, Switzerland

[21] Appl. No.: 517,024

[22] Filed: Jul. 25, 1983

[30] Foreign Application Priority Data

Aug. 12, 1982 [CH] Switzerland ............ 4835/82

[51] Int. Cl.³ .............. A61K 7/46; C07D 307/94; C07D 311/96
[52] U.S. Cl. ................. 252/522 R; 549/265
[58] Field of Search ............ 252/522 R; 549/265

[56] References Cited

FOREIGN PATENT DOCUMENTS 100935 2/1984 European Pat. Off. ............ 549/265
2405251 10/1977 France .

OTHER PUBLICATIONS

Bulletin de la Societe Chimique de France (1961), "Isomerisation photochimique dans la serie de l'alpha ionone", Compose IV, 1509–1512.

Chemical Abstracts, vol. 96, No. 25 (1982), p. 767, No. 218067f.

Primary Examiner—Anton H. Sutto
Attorney, Agent, or Firm—Scully, Scott, Murphy & Presser

[57] ABSTRACT

Spiro-lactones of formula

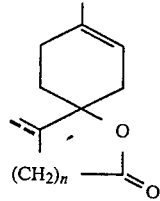

(I)

which could possess a supplemental bond at the position indicated by the dotted lines and wherein index n stands for integers 1 or 2, possess useful organoleptic properties and consequently can be utilized as perfume ingredients in the preparation of fragrance compositions and the perfuming of various articles such as e.g. soaps, cosmetics, detergents and household materials.

A process for their preparation starting from p-mentha-1,8-dien-4-ol is disclosed.

5 Claims, No Drawings

SPIRO-LACTONE DERIVATIVES, THEIR USE AS PERFUMING AGENTS, AND PERFUMING COMPOSITION CONTAINING SAME

BRIEF SUMMARY OF THE INVENTION

This invention relates to the field of perfumery; more particularly, it provides novel spiro-lactones of formula

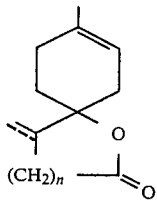

(I)

possessing or not a supplemental bond at the position indicated by the dotted lines and wherein index n stands for integers 1 or 2.

The invention provides further a fragrance composition containing as perfume active ingredient a spiro-lactone of formula (I).

This invention provides still further a method to improve, enhance or confer a coumarin type perfume character to fragrance compositions which comprises adding thereto a perfume effective amount of a spiro-lactone of formula (I).

Another object of this invention relates to a process for the preparation of spiro-lactones of formula (I), which process comprises:

a. adding ethylene oxide to p-mentha-1,8-dien-4-ol in the presence of a strong base, and b. oxidizing the thus obtained diol of formula

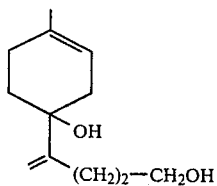

(II)

by means of pyridinium dichromate to give 9-methyl-5-methylene-1-oxaspiro[5.5]undec-8-en-2-one; or b'. reducing the said diol (II) to give a diol of formula

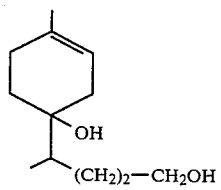

(III)

and c'. oxidizing this latter compound by means of pyridinium dichromate to give 5,9-dimethyl-1-oxaspiro[5.5]undec-8-en-2-one, or b". subjecting p-mentha-1,8-dien-4-ol to hydroformylation to give a compound of formula

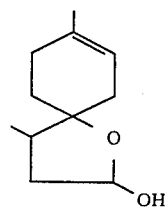

and c". treating the said compound with pyridinium dichromate to give 4,8-dimethyl-1-oxaspiro[4.5]dec-7-en-2-one.

THE INVENTION

We have discovered that the compounds of formula (I) possess useful organoleptic properties and that consequently they can advantageously be used as fragrance ingredients. Specific examples of the compounds of said formula (I) include the following preferred spiro-lactones:

5,9-dimethyl-1-oxaspiro[5.5]undec-8-en-2-one, 9-methyl-5-methylene-1-oxaspiro[5.5]undec-8-en-2-one and 4,8-dimethyl-1-oxaspiro[4.5]dec-7-en-2-one, all of which represent novel chemical compounds.

Their utilization in perfumery can be very wide. They may be used as perfume active ingredients in various types of compositions and can be utilized for the perfuming of a variety of articles ranging from soaps, cosmetics, shampoos, detergents, under their various forms, or household materials. Compounds (I) are also periodically suitable for imparting a fragrance to fabric softeners, especially in view of their substantivity. 9-Methyl-5-methylene-1-oxaspiro[5.5]undec-8-en-2-one and 4,8-dimethyl-1-oxaspiro[4.5]dec-7-en-2-one possess a spicy odor whose character is reminiscent of that of coumarin. Their effect is original in perfumery and compounds (I) become especially useful in the replacement of coumarin in certain of its applications.

5,9-Dimethyl-1-oxaspiro[5.5]undec-8-en-2-one possesses on the contrary a typical woody note reminiscent of cedar wood oil.

The proportions at which the compounds of the invention can achieve the desired effects can vary within a wide range. When used in the manufacture of bases or concentrates, preferred concentrations are of about 2–3% to 20% parts by weight of compounds (I) based on the total weight of the composition into which they are added, whereas when used to perfume articles such as soaps, cosmetics, hair-care articles, household materials or detergents, preferred concentrations are of the order of 0.2 to 1% by weight of the finished article.

The above given values of concentrations are not deemed to be interpreted restrictively. Those skilled in the art realize that the use of a given fragrance ingredient is dependent on the specific effects it is desired to achieve and on the nature of the coingredients in a given composition or of the material it is desired to perfume.

Compounds (I) can be utilized in their isolated form by direct addition to the article to be perfumed. Generally however they are used in admixture with other current perfume ingredients, diluents or supports.

As indicated above, the compounds of the invention are novel chemical entities. Their preparation occurs via a process utilizing p-mentha-1,8-dien-4-ol as starting material. The different steps of this process are effected according to per se known procedures. The process will be illustrated in a more detailed manner by the following examples and summarized by the reaction pathway given hereinbelow.

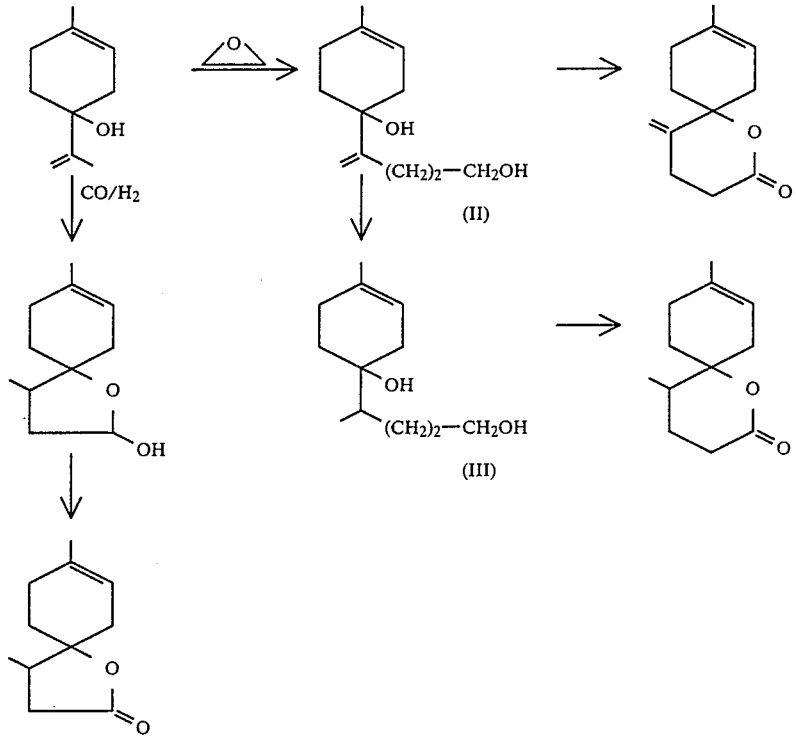

EXAMPLE 1

9-Methyl-5-methylene-1-oxaspiro[5.5]undec-8-en-2-one a. 4-[1-hydroxy-4-methyl-cyclohex-3-en-1-yl]pent-4-en-1-ol 551 G (4.75M) of N,N,N',N'-tetramethyl-ethylene-diamine (TMEDA) were added dropwise at room temperature to 2130 g (4.75M) of a 15% solution of butyl-lithium in hexane. The addition was slightly exothermic and the temperature of the reaction mixture raised to 45°. After having been kept at this temperature for 30 minutes, the mixture was cooled to 0° and 345 g of p-mentha-1,8-dien-4-ol in 500 ml of anhydrous ether were added thereto while the temperature was kept at 0° overnight. The brownish mass thus formed was dissolved in 500 ml of anhydrous THF and the resulting solution was cooled to −50°. 100 G (2.27M) of ethylene oxide were then added at this temperature during 5 h, whereupon the temperature of the mixture was raised to room temperature and stirring kept overnight. The hydrolysis of the mixture was effected by treating it with a concentrated solution of $NH_4Cl$. The organic phase was washed with a concentrated solution of NaCl until neutrality and, after evaporation, the residue was distilled on a Vigreux type column of 15 cm length. 177 G of the desired diol were thus obtained in a ca. 90% purity (yield: 63% based on converted p-mentha-1,8-dien-4-ol).

B.p. 130°–145°/1.33 Pa.

IR: 3350, 3033, 1645, 910 cm$^{-1}$;

MS: M$^+$ = 196(2); m/z: 178(8), 163(3), 111(67), 95(67), 84(49), 69(100), 55(73), 41(87).

b. 9-methyl-5-methylene-1-oxaspiro[5.5]undec-8-en-2-one

A mixture of 140 g (0.38M) of pyridinium dichromate, 16.5 g (0.084M) of the obtained diol (see letter a. above), and 600 ml of $CH_2Cl_2$ was kept stirring at room temperature for 18 h. A mixture of 300 ml of diethyl ether and 300 ml of petrol ether (30/50) was then added thereto and the resulting mixture was filtered. The clear filtrate was evaporated under vacuum and the residue distilled in a bulb apparatus (bath temperature: 150°). 10.3 G (yield 42%) of a product having about 65% purity were obtained.

IR (CDCl$_3$): 1730 cm$^{-1}$;

MS: M$^+$ = 192(35); m/z: 177(3), 164(8), 132(18), 124(35), 96(100), 81(19), 68(40), 55(32), 41(40);

NMR (60 MHz): 1.71 (3H, s); 2.00–2.06 (4H, 2s); 2.44 (2H, t); 2.63 (4H, s); 5.03 and 5.10 (2H, d); 5.33 (1H) δ ppm.

p-Mentha-1,8-dien-4-ol, used as starting material in the above described process can be obtained according to the procedure indicated by E. Girandi et al., Recherches, 19, 205 (1974).

EXAMPLE 2

5,9-Dimethyl-1-oxaspiro[5.5]undec-8-en-2-one a. 6.4 g of the diol obtained according to paragraph a. of Example 1 above, in 70 ml of ethyl acetate were hydrogenated in the presence of palladium on charcoal. After adsorption of 860 ml of hydrogen, the mixture was filtered and the clear filtrate was evaporated to give 6.2 g of a black oil.

b. A mixture of 6.0 g (0.03M) of the product obtained according to letter a. above, 40 g of pyridinium dichromate and 250 ml of dimethylformamide was kept under stirring in atmosphere of nitrogen during 16 h, whereupon it was diluted with water and extracted with several fractions of $CH_2Cl_2$. The combined extracts were washed with saturated NaCl, dried and evaporated. By distillation in a bulb apparatus, 3.15 g of an orange colored oil were obtained (bath temperature: ca. 150°; 1.33 Pa). The analytical characteristics of a purified sample were the following:

IR: 1735 cm$^{-1}$;

NMR (360 MHz): 1.025 and 1.04 (3H, 2d); 1.68 (3H, s); 5.26 (1H, s) δ ppm;

MS: M$^+$=194(60); m/z: 143(63), 121(34), 98(100), 93(90), 68(55), 55(60), 41(47).

EXAMPLE 3

4,8-Dimethyl-1-oxaspiro[4.5]dec-7-en-2-one a. 4,8-Dimethyl-1-oxaspiro[4.5]dec-7-en-2-ol 60 G of p-mentha-1,8-dien-4-ol, 0.09 g of HRhCO(PPh$_3$)$_3$ and 300 ml of cyclohexane were allowed to react for 4 h at 90° in an atmosphere of CO and H$_2$ at about 200 bar in an autoclave. After evaporation of the volatiles under reduced pressure, the residue was distilled to give a fraction at b.p. 90°–112°/4 Pa; 63.5 g. This product was fractionally distilled to give a pure product.

IR: 3420 cm$^{-1}$;

NMR: 0.95 (3H, d, J=6); 1.68 (3H, broad s); 5.38 (2H, m) δ ppm;

MS: M$^+$=182; m/z: 164(64), 149(10), 131(10), 108(18), 95(100), 79(70), 53(30), 41(57).

b. 4,8-Dimethyl-1-oxaspiro[4.5]dec-7-en-2-one

5 G (27.5 mM) of the product obtained according to paragraph a. above have been allowed to react with 11.3 g (30 mM) of pyridinium dichromate in 100 ml of methylene chloride. The mixture was kept 48 h under stirring at room temperature, whereupon the mixture was filtered and the clear filtrate evaporated and distilled in a bulb apparatus.

B.p. 120° (bath)/1.33 Pa; 5 g.

IR: 1770 cm$^{-1}$;

NMR: 1.05 (3H, d, J=6); 1.68 (3H, broad s); 5.3 (1H, broad s) δ ppm;

MS: M$^+$=180; m/z: 162(2), 120(15), 112(33), 93(32), 68(100), 42(63).

EXAMPLE 4

A proteinic shampoo was perfumed with 0.3 and 0.5% by weight of 9-methyl-5-methylene-1-oxaspiro[5.5]undec-8-en-2-one. The resulting product possessed a pleasant odor character which completely masked the disagreeable note of the base material.

EXAMPLE 5

A base perfume composition of lavender type was prepared by mixing the following ingredients (parts by weight):

| | |
|---|---:|
| Cinnamon oil of Ceylon, 10%* | 200 |
| Lavender oil | 180 |
| Geranium oil Bourbon | 100 |
| Vetyveryl acetate | 60 |
| Clove oil | 60 |
| Cedrene | 80 |
| Linalyl acetate | 40 |
| Benzyl benzoate | 60 |
| Galbanum gum 25%* | 20 |
| Synth. bergamot oil | 20 |
| Musk DTI[1] [4] | 20 |
| Exaltex ®[1] [3] | 20 |
| Tricyclone[1] [2] | 20 |
| Isoeugenol | 10 |
| Patchouli oil | 10 |
| | 900 |

*in diethyl phthalate
[1] origin: Firmenich SA, Geneva (Switzerland)
[2] see Swiss Pat. No. 626,532; 10,10-dimethyltricyclo[7.1.1.0$^{2,7}$]undec-2-en-4-one
[3] pentadecanolide
[4] 1,1-dimethyl-4-acetyl-6-tert-butylindane By adding to the above base composition 9-methyl-5-methylene-1-oxaspiro[5.5]undec-8-en-2-one in a 10% by weight proportion, a novel composition resulted whose odorous character was richer, more elegant and harmonious than that of the base composition.

The spicy note became fuller without possessing the aggressiveness shown by a composition obtained by replacing the said spiro-lactone by coumarin.

By adding, in a 10% proportion, a mixture constituted by equal amounts of the said spiro-lactone and coumarin, a novel composition resulted whose odorous character was preferred over that shown by the addition of one of the other of said isolated ingredients. This implies that 9-methyl-5-methylene-1-oxaspiro[5.5]undec-8-en-2-one combines well with coumarin and enhances successfully its spicy character.

What we claim is:

1. A method to improve, enhance or confer a coumarin type perfume character to fragrance compositions which comprises adding thereto a perfume effective amount of a compound selected from the group consisting of 5,9-Dimethyl-1-oxaspiro[5.5]undec-8-en-2-one, 9-Methyl-5-methylene-1-oxaspiro[5.5]undec-8-en-2-one and 4,8-Dimethyl-1-oxaspiro[4.5]dec-7-en-2-one.

2. A fragrance composition containing as perfume active ingrdient a compound selected from the group consisting of 5.9-Dimethyl-1-oxaspiro[5.5]undec-8-en-2-one, 9-Methyl-5-methylene-1-oxaspiro[5.5]undec-8-en-2-one and 4,8-Dimethyl-1-oxaspiro[4,5]dec-7-en-2-one.

3. 5,9-Dimethyl-1-oxaspiro[5.5]undec-8-en-2-one.

4. 9-Methyl-5-methylene-1-oxaspiro[5.5]undec-8-en-2-one.

5. 4,8-Dimethyl-1-oxaspiro[4.5]dec-7-en-2-one.

* * * * *